(12) United States Patent
Gelfand et al.

(10) Patent No.: US 9,907,487 B2
(45) Date of Patent: Mar. 6, 2018

(54) NON-INVASIVE METHOD AND APPARATUS FOR DETERMINING LUNG TISSUE THERMAL PROPERTIES AND FOR EXTRA VASCULAR LUNG WATER MEASUREMENT

(71) Applicants: Alexander Gelfand, Hadera (IL); Konstantin Goulitski, Holon (IL)

(72) Inventors: Alexander Gelfand, Hadera (IL); Konstantin Goulitski, Holon (IL)

( * ) Notice: Subject to any disclaimer, the term of this patent is extended or adjusted under 35 U.S.C. 154(b) by 363 days.

(21) Appl. No.: 14/602,298

(22) Filed: Jan. 22, 2015

(65) Prior Publication Data
US 2016/0213330 A1 Jul. 28, 2016

(51) Int. Cl.
*A61B 5/08* (2006.01)
*A61B 5/00* (2006.01)
*A61B 5/01* (2006.01)

(52) U.S. Cl.
CPC .............. *A61B 5/08* (2013.01); *A61B 5/4878* (2013.01); *A61B 5/01* (2013.01)

(58) Field of Classification Search
CPC ......... A61B 5/08; A61B 5/0803; A61B 5/082; A61B 5/083; A61B 5/087; A61B 5/0878; A61B 5/01
USPC ................................................ 600/529, 532
See application file for complete search history.

(56) References Cited

U.S. PATENT DOCUMENTS

| | | | | |
|---|---|---|---|---|
| 4,230,126 A * | 10/1980 | Elings | ...................... | A61B 5/01 600/484 |
| 4,488,559 A * | 12/1984 | Iskander | .................. | A61B 5/05 600/430 |
| 5,005,582 A | 4/1991 | Serikov et al. | | |
| RE34,938 E * | 5/1995 | Serikov | ..................... | A61B 5/01 600/504 |
| 6,488,677 B1 * | 12/2002 | Bowman | .................. | A61B 5/01 600/549 |

(Continued)

OTHER PUBLICATIONS

Eisenberg, et al., A Prospective Study of Lung Water Measurements during Patient Management in an Intensive Care Unit, Am Rev Respir Dis, 1987, pp. 662-668, vol. 136.

(Continued)

*Primary Examiner* — Kristen Matter
(74) *Attorney, Agent, or Firm* — Browdy and Neimark, P.L.L.C.

(57) ABSTRACT

The subject matter discloses a noninvasive method and device for detection, measurement and monitoring of Pulmonary Interstitial fluid—Extravascular Lung Water —volumes in inpatient settings: Intensive Care Units, Emergency Rooms, Internal Hospital Departments, and daily monitoring of chronic patient in outpatient settings: outpatient departments, rehab centers and Home monitoring. The disclosed method is based on the analysis of lung tissue thermodynamic properties, and their deviation from normal value. The device measures the rate of temperature change of a lung tissue by measuring the exhaled gas temperature changing rate during cooling/heating of lung tissue. The cooling/heating of lung tissue may be achieved by prompt changing one of the inhaled gas parameters temperature, and/or humidity, and/or rate of breathing, and/or tidal volume, and/or type of gas and etc. The change is performed at the beginning of measurement, and is kept during entire measurement time.

8 Claims, 13 Drawing Sheets

(56) References Cited

U.S. PATENT DOCUMENTS

| | | | | |
|---|---|---|---|---|
| 9,364,158 B2* | 6/2016 | Banet | ............ | A61B 5/01 |
| 2015/0059764 A1* | 3/2015 | Metelits | ............ | A61M 16/0677 |
| | | | | 128/207.18 |
| 2017/0182279 A1* | 6/2017 | Power | ............ | A61M 16/14 |

OTHER PUBLICATIONS

Mitchell, et al., Improved Outcome Based on Fluid Management in Critically Ill Patients Requiring Pulmonary Artery Catheterization, Am Rev Respir Dis, 1992, pp. 990-998, vol. 145.

* cited by examiner

NON-INVASIVE METHOD AND APPARATUS FOR DETERMINING LUNG TISSUE THERMAL PROPERTIES AND FOR EXTRA VASCULAR LUNG WATER MEASUREMENT

FIELD OF THE INVENTION

The present disclosure relates to determination the difference of human lungs' thermal tissue properties from the normal value and detection, measurement and monitoring of Pulmonary Interstitial fluid—Extra Vascular Lung Water (EVLW)—volumes.

BACKGROUND OF THE INVENTION

Detection, monitoring and measurement of EVLW (Extravascular Lung Water) are matters of interest for decades. Non-invasive, instant and reliable EVLW measurement method is expected to be superior to existing procedures like blood oxygenation, chest radiography, minimally invasive trans-pulmonary thermodilution for assessment of pulmonary edema.

EVLW was suggested as a predictor of mortality in patients with severe sepsis and Acute Lung Injury (ALI) as a diagnostic tool in detecting early pulmonary edema and in evaluating the effect of ventilator modes during esophagectomy. The measurement has also been proposed to guide fluid therapy in acute respiratory distress syndrome and subarachnoid hemorrhage, and to assess the effect of steroids during cardiac surgery. EVLW was the primary outcome variable in clinical trials to study the efficacy of salbutamol to resolve pulmonary edema in patients with ALI/acute respiratory distress syndrome (the Beta-Agonist Lung Injury Trial) and lung resection.

In patients with acute exacerbations of chronic left heart failure or with acute myocardial infarction, hydrostatic pulmonary edema frequently develops leading to hypoxemia and decreases in lung compliance and ultimately to respiratory failure. Resolution of edema from the alveolar space predicts outcome and is essential for survival in ALI. There are evidences that suggest that a strategy to limit or reduce the amount of extra-vascular lung water (EVLW) from all reduces mortality in and improves the quality of life of patients suffering from EVLW due to preventing treatment. These studies provide strong evidence to support the direct measurement of EVLW in patients in whom a clinical suspicion of pulmonary edema exists, or in those felt to be at risk to develop pulmonary edema and that treatment strategy be specifically designed around attempting to lower elevated EVLW to normal goals.

Eisenberg et al and Mitchell et al in two separate studies (1987 and 1992), first demonstrated that when fluid and hemodynamic management is guided by measured EVLW as opposed to central pressures and usual care, outcome is significantly improved. EVLW fell to a greater extent in patients with ALI and in patients with heart failure and the duration of time spent on the ventilator and in the ICU was less in both studies.

Among the various methods for measurement of EVLW, thermo-dye dilution has been used most frequently. In critically ill patients, fluid management guided by thermo-dye measured EVLW was associated with improved clinical outcome. Hence, EVLW has been suggested to play a role as an independent predictor of the prognosis and course of illness. However, the thermo-dye dilution method is relatively time consuming, cumbersome and expensive. For these reasons, the method has not gained general acceptance.

Use of a technique based on injection of a single thermo-indicator that can be detected using an indwelling arterial catheter was an appealing concept. Recent experimental and clinical studies have shown that EVLW assessed by single thermodilution (ST) exhibits good reproducibility and close agreement with the thermo-dye double indicator technique. The invasiveness of the procedure is the main problem that prevents wide clinical use of this procedure. Thermodilution technique requires insertion a catheter in to the central vein and peripheral artery for indicator injection and collection of thermo-dye. Catheterization and puncturing of large blood vessels are complicated procedures often accompanied by various complications and cannot be recommended as routine procedures.

U.S. Pat. No. 5,005,582 discloses a non-invasive method for measuring pulmonary blood flow and lung tissue volume, called airway thermal volume consisting of dynamic registration of respiratory heat losses in ventilatory loading and/or humidity and temperature changes of the inspired gas. Pulmonary blood flow and airway tissue volume are calculated by solving the differential equation for non-steady-state heat and mass exchange between the lungs and the environment. The lungs fraction as natural conditioner of the inspired air, having an inner heat source (pulmonary blood flow) and an outgoing heat stream calculated by measuring the volume ventilation and the temperature and humidity of inspired and expired. air. Alterations of the baseline steady-state condition of lung respiratory heat exchange with the environment by changes in ventilation lead to achievement of a new steady-state condition where the heat stream from the lungs into environment is balanced by the heat stream from the circulation into the lung tissue. The maximal temperature of the expired air is taken as an initial relative value of lung tissue temperature, so that the quantity of maximal expired temperature change between two different steady-state conditions of lung heat exchange is proportional to the pulmonary blood flow, while the rate at which the new steady-state is achieved is proportional to the quantity of tissue mass. A probe for carrying out measurements includes a low-inertial device for temperature and humidity measurements of the expired and inspired air located in the middle of the airstream near the entrance to the upper respiratory tract, combined with a device for gas volumetric measurements and valves dividing in—and out-flowing air for minimizing errors in air temperature and humidity measurements

SUMMARY OF THE INVENTION

The subject matter discloses a noninvasive method and device for detecting measurement and monitoring Extravascular Lung Water in inpatient settings—Intensive Care Units, Emergency Rooms, Internal Hospital Departments, and daily monitoring of chronic patient in outpatient settings—outpatient departments, rehab centers and Home monitoring. The disclosed method is based on the measurement and the analysis of lung tissue thermal properties' deviation from normal value. The device measures the rate of temperature change of a lung tissue by measuring the exhaled gas temperature changing rate during cooling/heating of lung tissue. The cooling/heating of lung tissue may be achieved by prompt changing one of the inhaled gas parameters temperature, and/or humidity, and/or rate of breathing, and/or tidal volume, and/or type of gas and etc. The change is performed at the beginning of measurement, and is kept during entire measurement time.

Lungs are the natural heat exchanger with an internal heat source (pulmonary blood flow) and coolant (inhaled and exhaled gas). Since the breathing gas temperature is related to the lung tissue temperature through the convective heat transfer, inhaled gas can change the lung tissue temperature, and exhaled gas characterizes the temperature change of the lung tissue. Therefore the cooling/heating of the lung tissue can by activated by prompt changing and keeping constant of the temperature of inhaled gas or other parameter mentioned above, while changing of temperature of exhaled gas will corresponds to changing of temperature of the lung tissue at side of gas flow. The amount of heat that potentially can be received from blood flow is approximately ten times more than amount of heat that can be dissipated through breathing gas flow, thus the change of lung tissue temperature at the side of blood flow is negligible.

The rate of the lung tissue temperature being changed at cooling/heating depends on the thermal properties of the lung tissue, the thermodynamic properties of conductive airways' walls, heat-transfer conditions on the respiratory tract surface and lung's geometrical form. The inventors found that due to the geometrical similarity of human lungs and the similarity of thermodynamic properties of normal lung tissue, walls of conductive airways and heat-transfer conditions on these walls, the rate of the lung tissue temperature change during cooling/heating of all normal/healthy individuals is the same; thus, the deviation in the changing rate of exhaled gas temperature from the norm, characterizes changes in the thermodynamic properties of lung tissue, conductive airways walls' and heat-transfer conditions on the walls' surface. Accumulation of extravascular lung water leads to the change of thermal properties of lung tissue, and, affects the rate of exhaled gas temperature change.

According to some embodiments, the method includes measuring the temperature of the exhaled gas and calculation of a parameter related to lungs' tissue thermal properties during the transient state of heat transfer. The measuring can be performed during spontaneous or ventilated breathing. The transient state of heat transfer is achieved by the change in properties of inhaled gas change of inhaled gas temperature, and/or humidity, and/or concentration, and/or changing mixture of gases; or by the change in breathing pattern tidal volume and/or respiratory rate. The parameter related to lungs' thermal properties is calculated from the exhaled gas temperature changing rate; then the extravascular lung water is determined in accordance with correlation function that relates the difference between the determined lungs' thermal properties from its normal value and the amount of extravascular lung water.

According to some embodiments, the method comprises direct measurement of lung tissue thermal properties that are changed as result of accumulation of pulmonary interstitial fluid. According to some embodiments the method and system is based on a known phenomenon of regular regime of heating or cooling of the body which is determined by the rate of change in body temperature; wherein the rate of change in body temperature depends on the body's thermal properties.

One technical problem dealt with by the present disclosure is to how to shorten the period of the measuring of Extravascular Lung Water. Method known in the art such as the method disclosed in U.S. Pat. No. 5,005,582 requires the measuring of the entire transferred heat quantity between the blood flow and the air flow in a time period from one steady state to another. This period could be up to few minutes. In ventilated patients such lengthy time may lead, in some cases, to hyperventilation. Such known in the art methods are also not effective in spontaneously breathing patient due to relatively prolonged measurement time.

One technical solution is a non-invasive method and apparatus for determining lung tissue thermal properties and for measuring extra vascular lung water. The method comprising measuring temperature and flow gas inhaled by a patient; wherein properties of the inhales gas being changed during the inhaling and during the measuring; measuring temperatures and flow of gas exhaled by the patient changing the properties of the inhales gas when the patient inhales the gas calculating rate of change of the temperature of the exhaled gas and determining extravascular lung water volume for the calculated rate. This method requires up to ten breathing cycles only.

The method can be used in ventilated patients and in spontaneously breathing patients because it is not expected to overload the patient lungs. Measurement can be performed with a short break that allows tracking the tissue thermal properties—lungs health condition—with high temporal resolution without causing any harm or inconvenience to the patient.

Such a method defines a basic normal value of lung tissue thermal properties for all healthy individuals, which does not depend on other bio-physiological parameters. This allows measurement of the amount of accumulated lung fluid in every patient, without knowing initials characteristic of patient's lung tissue thermal properties.

Such a method does not depend on external environmental conditions such as temperature, pressure and humidity, as well as on the initial patient physiological conditions, body temperature, blood pressure, blood flow rate, breathing rate and etc. Short measurement time and quantitative output enable the device to be effectively used in inpatient settings like Intensive Care Units, Emergency Rooms and internal Hospital Department as well as in outpatient settings like outpatient departments, rehab centers and patient home (Home Monitoring).

One exemplary embodiment of the disclosed subject matter is a non-invasive method for determining lung tissue thermal properties and for measuring extra vascular lung water. The method comprising measuring first temperatures or first flow of gas inhaled by a patient; wherein properties of the inhales gas being changed while the measuring; as a result of the changing properties, measuring second temperature or second flow of gas exhaled by the patient; calculating rate of change of the second temperature or the second flow of the exhaled gas the rate of change being relative to change of the first temperature or the first flow; and determining extravascular lung water volume in accordance with the calculated rate of change.

According to some embodiment, the method further comprises changing properties of the inhaled gas. According to some embodiment, the method further comprising calculating the amount of the extra vascular lung water in accordance with a correlation function. According to some embodiment the method wherein the properties being one member of a group consisting of temperature, humidity, rate of breathing tidal volume and type of gas. According to some embodiment, the measuring is being for up to ten breathing cycles.

One other exemplary embodiment of the disclosed subject matter is a non-invasive apparatus for determining lung tissue thermal properties and for measuring extra vascular lung water volume the apparatus comprises: a sensor (2) adapted for measuring first temperatures of gas inhaled by a patient or a sensor (3) adapted for measuring first flow of gas inhaled by the patient; wherein properties of the inhales gas being changed while the measuring; and a processing unit (7) being configured for calculating rate of change of second temperature or the second gas flow; wherein the rate of change being relative to change of the first temperature or the first flow; wherein the processing unit (7) being farther configured for determining extravascular lung water in accordance with the calculated rate. According to some embodiments, the apparatus farther comprising a humidifier [22] being adapted for controlling the properties of the inhaled gas. According to some embodiments the patient being ventilated or non-ventilated. According to some embodiments wherein the apparatus being configured for measuring up to ten breathing cycles.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

Figure 12:
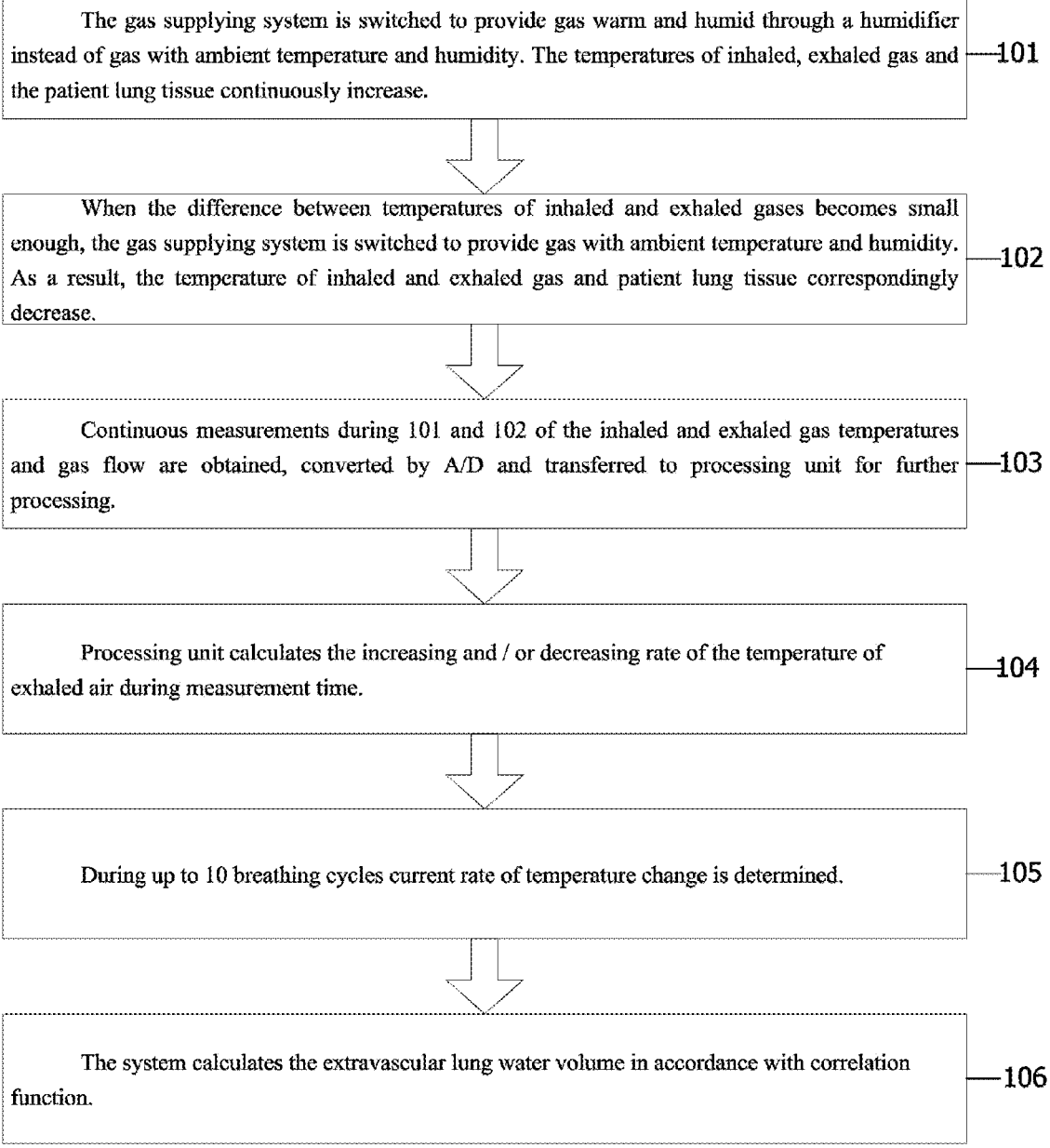
Figure 13:
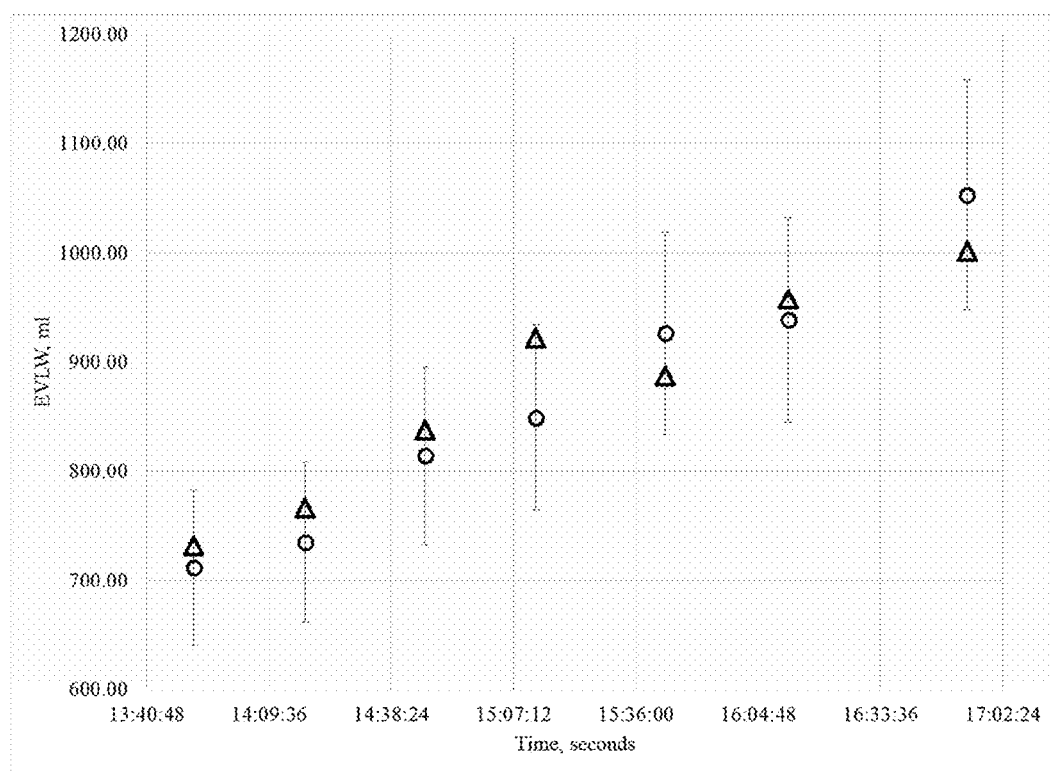

FIG. 12 shows a method for determination extra vascular lung water for ventilated patients, in accordance with some embodiments of the disclosed subject matter; and FIG. 13 shows correlation between measurement of extravascular lung water by conventional thermo-dilution method and by the non-invasive method for extra vascular lung water measurement according to some embodiments of the disclosed subject matter.

DETAILED DESCRIPTION

Figure 1:
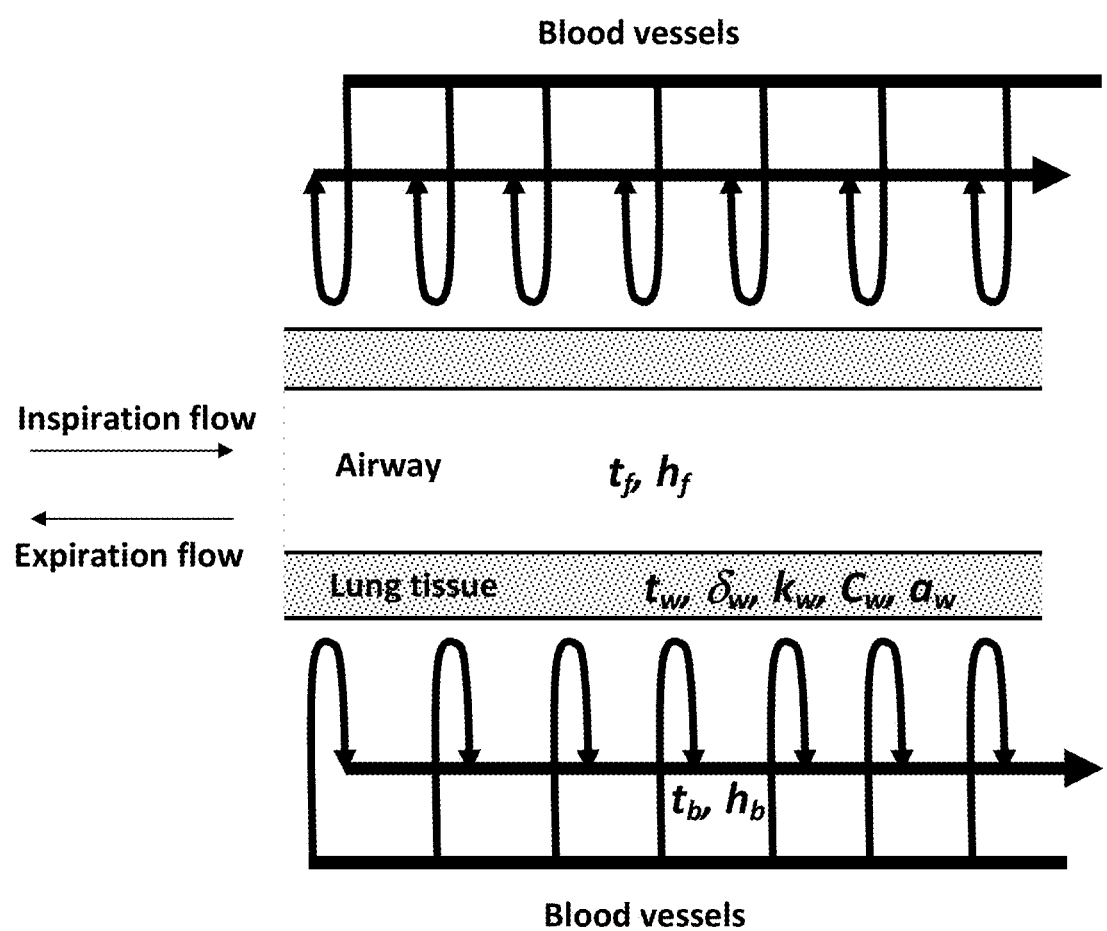
FIG. 1 shows a scheme of lung's heat exchanger, in accordance with some embodiments of the disclosed subject matter.

FIG. 1 shows a scheme of lung's heat exchanger, in accordance with some embodiments of the disclosed subject matter. Human lungs serve as gas-exchanger and as body-environment heat-exchanger as well, where the heat is transferred from blood flow to airflow through lung tissue. The pulmonary blood flow is considered as heat source, and the breathing airflow is considered as the coolant. The air flow dissipates heat from the walls of the conductive airways and alveoli, with convective heat transfer coefficient $h_f$, which depends on the airways' wall tissue surface properties and gas flow rate. The rate of heat conductivity through the wall is characterized by diffusivity coefficient $a_w$, which is expressed through thermal conductivity coefficient $k_w$, density $\rho_w$ and specific heat capacity coefficient $C_w$ of a wall—i.e. on the thermal properties of the lung tissue.

The thermal resistance of heat flux from the blood flow—$1/h_b$—is approximately in ten times less than thermal resistance $\delta/k_f$ of the lung tissue wall and the thermal resistance—$1/h_f$—of heat flux from the wall of the conductive airways to the airflow. Therefore, according to the theory of heat transfer through wall, the changes of the thermal properties of the lung tissue, through which heat is transferred and changes in the conditions of heat convection from the surface of the conductive airways in the airflow, mainly affect the heat transfer.

Normally the lungs stay in thermal equilibrium and the heat transfer is in the steady-state condition. When one of breathing parameters changes, the thermal equilibrium destabilized and heat transfer in the lung's heat exchanger gets into the transient condition, thus process of lung tissue cooling or heating starts. Thermal equilibrium could be destabilized by a) change of inhaled gas temperature, and/or humidity, and/or concentration, and/or changing mixture of gases, b) variation of the respiratory rate, c) variation of tidal volume.

When the inhaled gas property has been kept changed for some time, the temperature of the lung tissue changes during the cooling/heating until the heat transfer in the lung's heat exchanger reaches the a new steady-state condition (thermal equilibrium). Since the temperature of breathing gas is related to the lung tissue temperature through the convective heat transfer, the temperature of the exhaled gas flow characterizes the temperature changing of the lung tissue.

It is known from the heat transfer theory that the Fourier equation derived for temperature difference $\partial$ between any point in the body $t_w$ and the ambient fluid $t_f$ has the form $$\frac{\partial \vartheta}{\partial \tau} = a \nabla^2 \vartheta, \quad (1)$$

where, $\vartheta = t_w - t_f$ is the excessive body temperature, $\tau$—is time, and $a = k/(C\rho)$—is the heat diffusivity coefficient.

In accordance with main theorem of regular regime, the general integral of Fourier equation (1) for the problem of cooling of homogeny and isotropic body of any form, can be expressed by infinity series, where its items are exponential quickly decreased functions of time:

$$\vartheta = A_0 U_0 e^{-m_0 \tau} + A_1 U_1 e^{-m_1 \tau} \ldots A_i U_i e^{-m_i \tau}, \quad (2)$$

where the positive numbers $m_0, m_1, m_i, \ldots, m_n$ are series of continuously increasing numbers:

$$0 < m_0 < m_1 < m_2 < m_i \ldots m_n, \quad (3)$$

$U_0, U_1, U_i, \ldots U_n$—functions of point coordinates, and $A_0, A_1, A_i, \ldots A_n$ also finite constant numbers, independent to time and coordinates.

When we consider time points that move away from the initial point, then the members of series (2) are decreasing by absolute value. Beginning from the second member, which corresponds to i=1, series members become negligibly small in comparison to the first series member. Therefore the temperature $t_w$ in any point of a body will be expressed by the first member of series (2) long before as it will become equivalent to $t_f$. Thus it is determined by the exponential law:

$$t_w - t_f = \vartheta = A_0 U_0 e^{-m\tau} \quad (4)$$

where m—minimal value of numbers $m_0, m_1, m_2, \ldots$

Thermal regime, characterized by expression (4), can be considered as regular regime of cooling or heating.

Taking the logarithm of (4) we obtain:

$$\ln|\vartheta| = -m\tau + G(x,y,z), \quad (5)$$

where G(x, y, z)—is function of point coordinates, after differentiation obtain $$-\frac{\partial(\ln|\vartheta|)}{\partial \tau} = m \quad (6)$$

The main property of all cooling/heating processes can be formulated as following:
a) the regular regime in incipient during the limited time after starting of cooling/heating;
b) the logarithm of the difference between temperature $t_w$ in any point of a body and the temperature of ambient fluid $t_f$ changes with time τ by a linear law;
c) the logarithm of excessive temperature change rate–m– is similar for all body points.

These properties relate to a body of any form complexity, with any heat transfer coefficient, and any initial conditions. Hence when the rate of logarithm of temperature changing of the exhaled gas flow has linear character during, described above, transient state condition of the heat transfer in the lung's heat exchanger then the rate of logarithm of temperature changing of the lung tissue is also linear. In this case the cooling/heating can be considered as regular and its rate characterizes the properties of lung tissue, the properties of the conductive airways walls tissue and heat-transfer conditions on the walls' surface.

The similarity of the geometrical lungs' structure, properties of lung tissue, properties of the conductive airways walls tissue and heat-transfer conditions on the walls' surface for normal (healthy) lungs allows considering the rate of temperature changing at cooling/heating as similar for a variety of normal (healthy) individuals. Thus, the difference between measured rate of temperature changing at cooling/heating and its normal value can be considered as a parameter which determines the changes of lungs tissue thermal properties and/or changes of heat transfer conditions from the walls of conductive airways.

Figure 2:
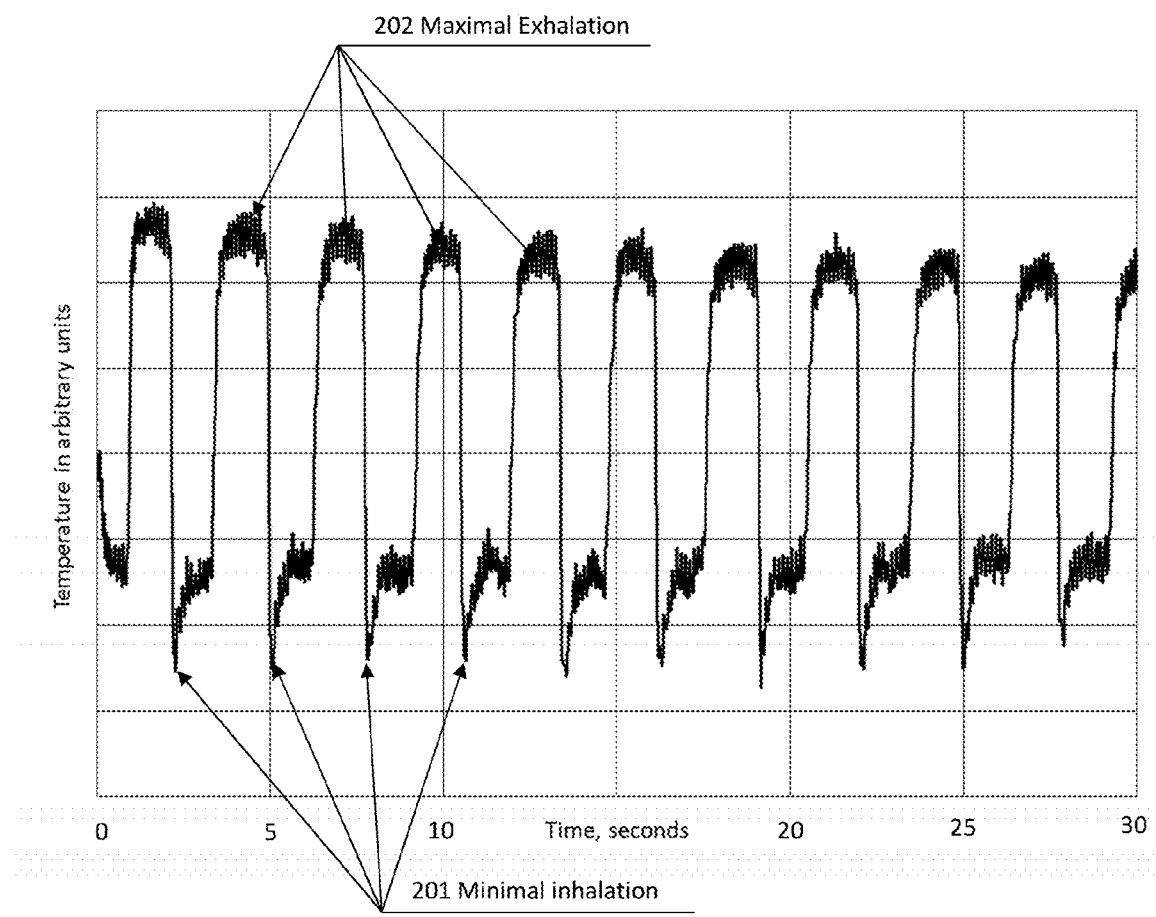
FIG. 2 shows typical curve of temperatures of inhaled and exhaled gas measured when breathing with cooled air, in accordance with some embodiments of the disclosed subject matter.

FIG. 2 shows typical curve of temperatures of inhaled and exhaled gas measured when breathing with cooled air, in accordance with some embodiments of the disclosed subject matter. The curve of the measured temperature of the inhaled and exhaled air at the mouthpiece is shown when inhaled gas's temperature was promptly changed at the beginning and has been kept up to the finish of the measurement. The temperature of inhaled gas is approximately constant as it can be observed from the minimal inhaled temperature points 201. The temperature of exhaled gas decreases as can be observed from maximal exhaled temperature points 202. The exhaled gas temperature change indicates decreasing temperature of the lung tissue.

Figure 3:
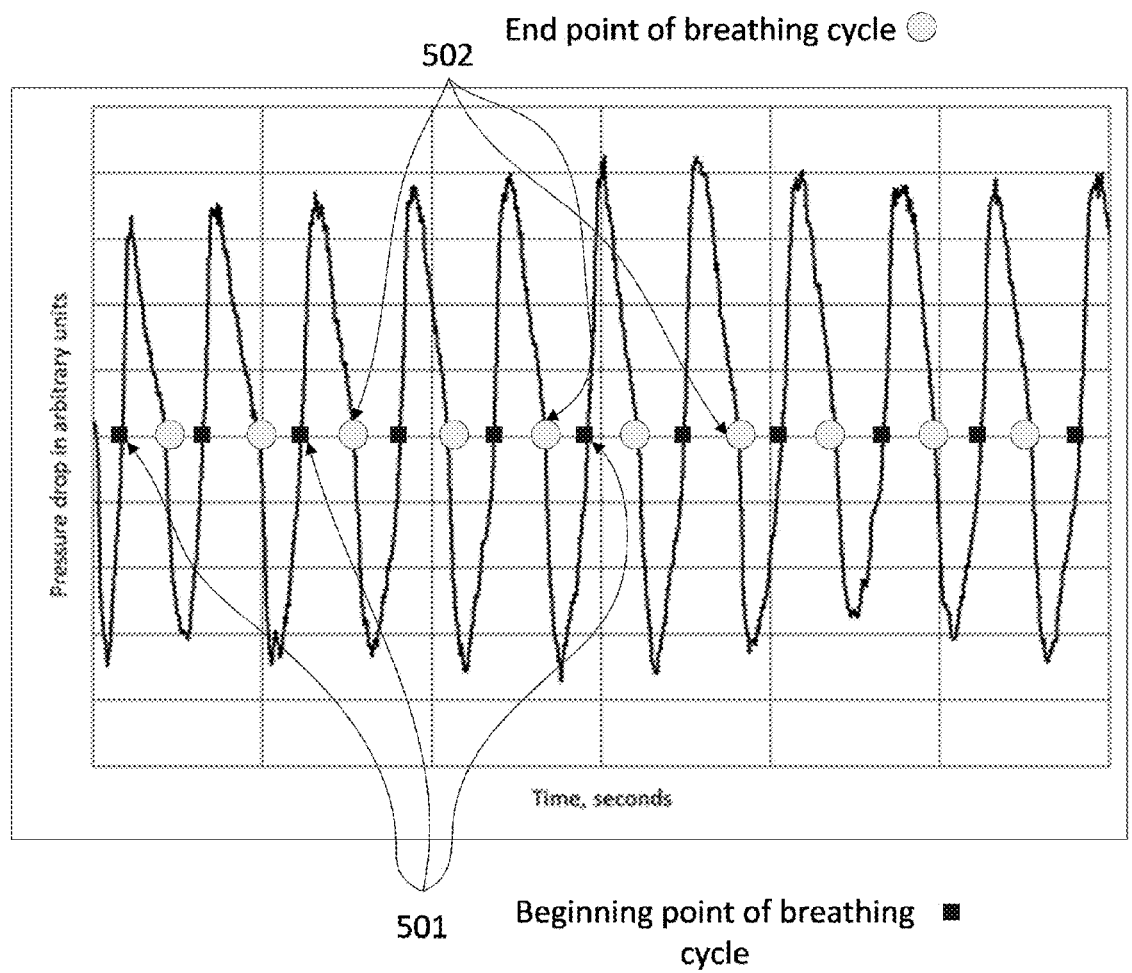
FIG. 3 shows typical graph of pressure drop changes of inhaled and exhaled air flow measured during breathing by using flow meter, in accordance with some embodiments of disclosed subject matter.

FIG. 3 shows typical graph of pressure drop changes of inhaled and exhaled air flow measured during breathing by using flow meter, in accordance with some embodiments of disclosed subject matter. The curve is used for determination of the beginning breathing cycle time points [501] and the end breathing cycle time points [502] of breathing cycles. The beginning and end points of breath cycles are used in order to determine the time points where the temperature of exhaled air is processed.

Figure 4:
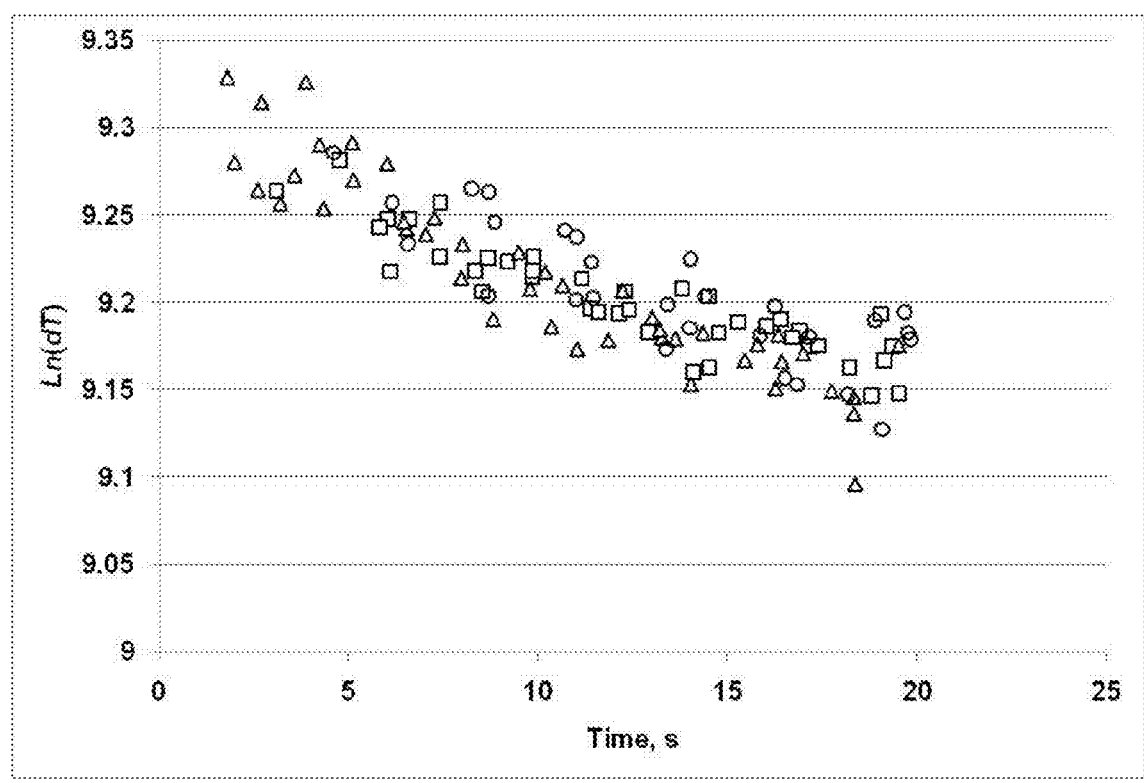
FIG. 4 shows typical graph of changes in time of natural logarithm of excessive exhaled gas temperature for healthy lungs, in accordance with some embodiments of the disclosed subject matter.

FIG. 4 shows typical graph of changes in time of natural logarithm of excessive exhaled gas temperature for healthy lungs, in accordance with some embodiments of the disclosed subject matter. According to described above theory of regular regime, the rate of excessive temperature change during cooling/heating has a logarithmic character. Presented results introduce temperature measurements of several normal (healthy) individuals. The graph shows that the rates of exhaled gas temperature's changes of all individuals can be described by a same linear function. This fact reinforces the claim that the rate of temperature's changing is similar for different normal (healthy) lungs.

Figure 5:
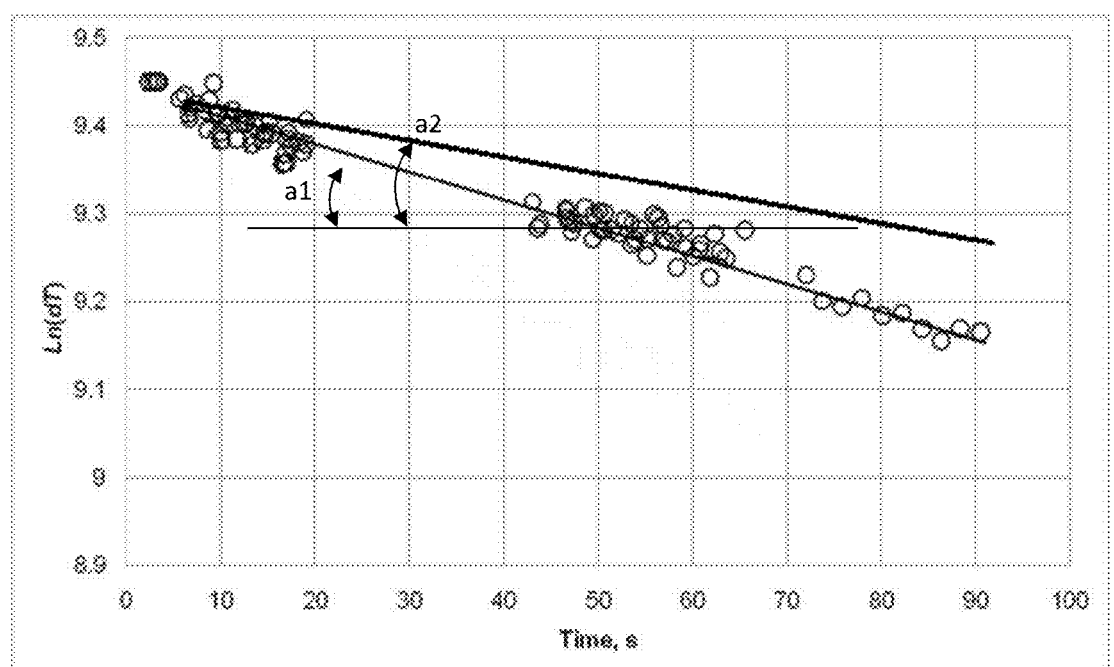
FIG. 5 shows a scheme for measuring of the differences between normal and abnormal rates of cooling which is taken at a certain time from the start of measurement, in accordance with some embodiments of the disclosed subject matter.

FIG. 5 shows a scheme for measuring of the differences between normal and abnormal rates of cooling which is taken at a certain time from the start of measurement, in accordance with some embodiments of the disclosed subject matter. The cooling/heating rate deviation from the normal value can be determined, by difference between slops (a1–a2) of the logarithm functions of the excessive temperature of exhaled gas of two measurements: measurement corresponded to a normal lung and some current measurement. Measurements can be performed for spontaneously breathing or ventilated patients.

Figure 6:
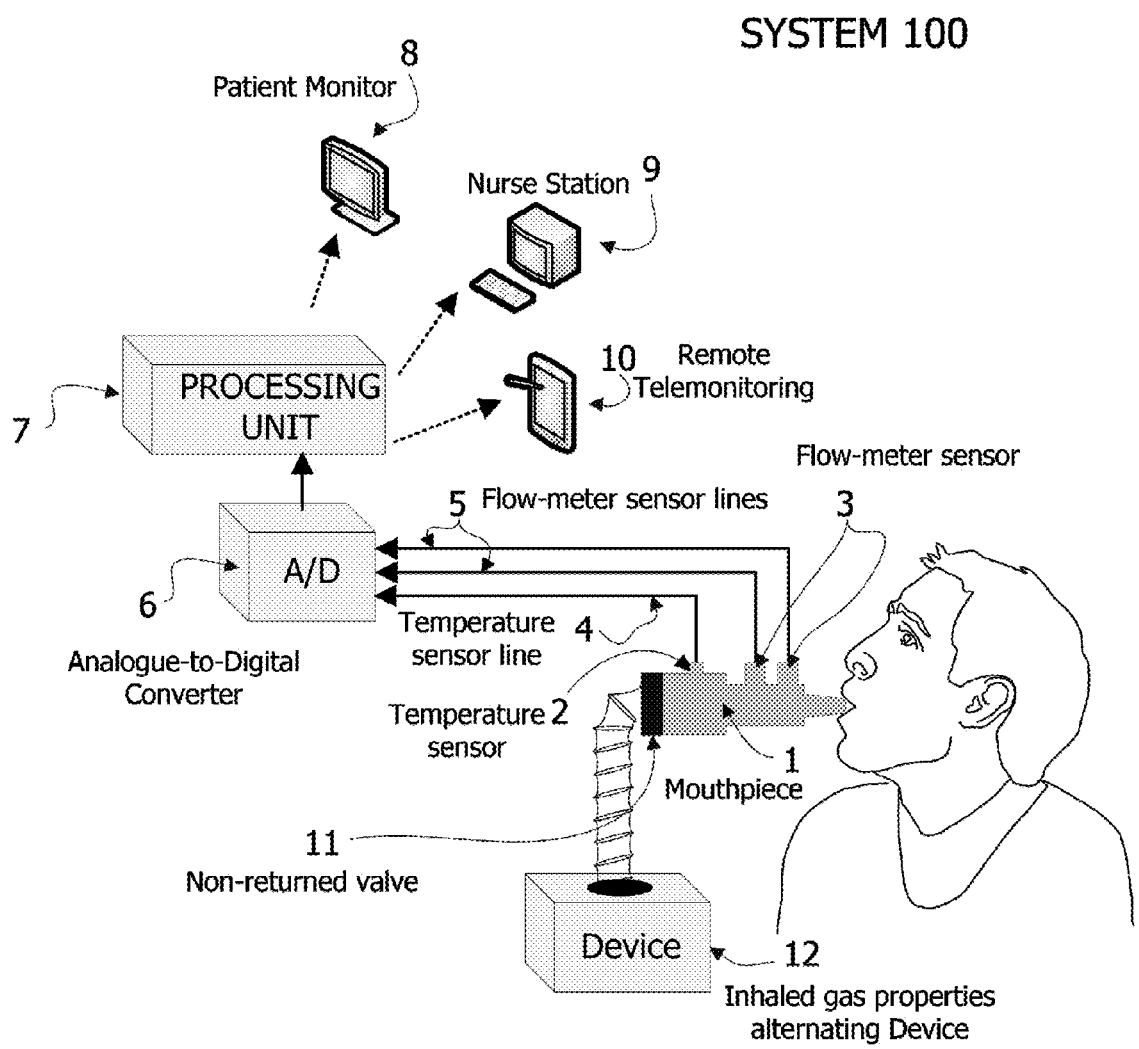
FIG. 6 shows a schematic diagram of a system for spontaneously breathing patients, in accordance with some embodiments of the disclosed subject matter.

FIG. 6 shows a schematic diagram of a system for spontaneously breathing patients, in accordance with some embodiments of the disclosed subject matter. System [100] includes mouthpiece [1] with incorporated gas temperature sensor [2], gas flow meter [3] which is based on measurement of a pressure drop or any other sensor allowing determination of gas flow. Pressure drop and temperature signals are transferred via temperature sensor line [4] and flow-meter sensor lines [5] and captured by an analog-to-digital converter [6], which transfers the converted data to the processing unit [7]. The processing unit [7] calculates rates of temperature change of the exhaled air and determines and/or calculates the extra vascular lung water volume from this rate. In one embodiment the changing of the temperature of the exhaled air is performed with a device [12] that alternates properties of inhaled gas, such as temperature (conditioner), humidity (humidifier) or mixture composition (gas-mixer). In one other embodiment the measurement is performed without a device [12] by asking the patient to change the breathing rate. To ensure the separation of inhaled and exhaled gases' flows, there is non-returned valve [11] installed in the gas supplying system. In one embodiment the reprocessed data is stored and displayed on bedside computer and is displayed on Patient Monitor [8]; In one other embodiment the reprocessed data is stored in Hospital Information System in appropriate format (for example DICOM-compatible) and is displayed on nurse/doctor working station [9]; In yet one other embodiment the reprocessed data is sent to remote telemedicine center [10] for further processing.

Figure 7:
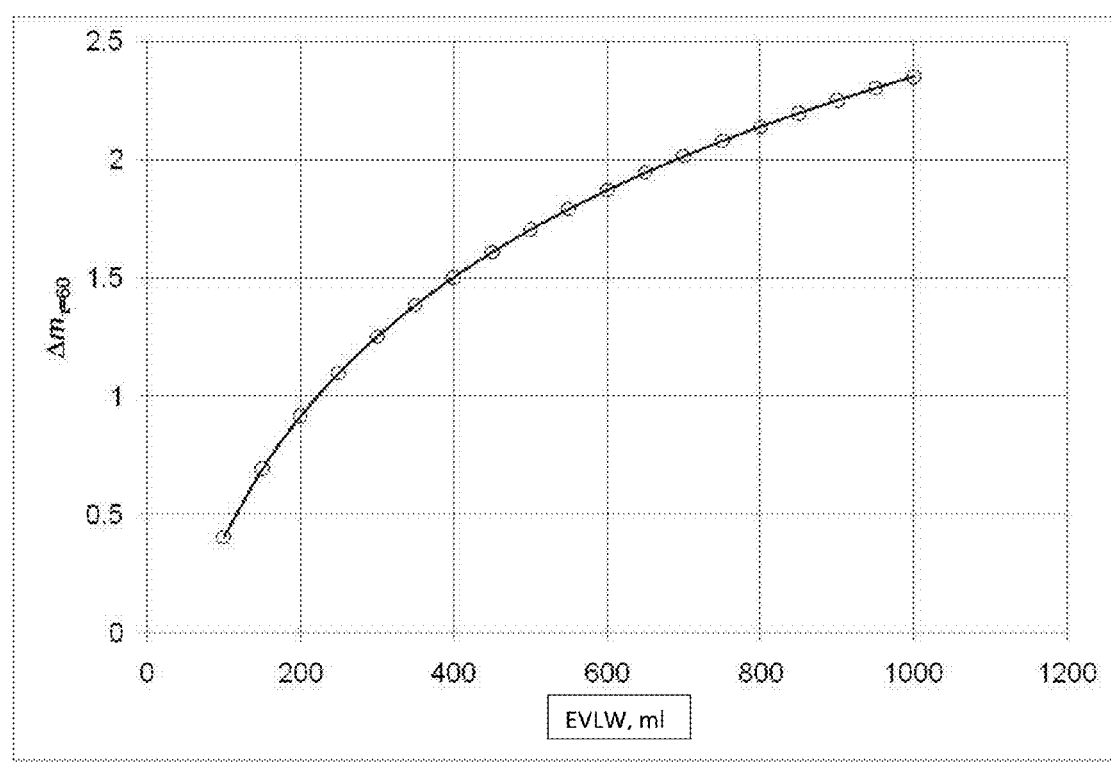
FIG. 7 shows a schematic correlation between the amount of EVLW and the magnitude of the differences between normal and abnormal rate of cooling/heating at a particular time of measurement, in accordance with some embodiments of the disclosed subject matter.

FIG. 7 shows a schematic correlation between the amount of EVLW and the magnitude of the differences between normal and abnormal rate of cooling/heating at a particular time of measurement, in accordance with some embodiments of the disclosed subject matter. The figure relates the deviation of the cooling/heating rate with an EVLW volume.

Figure 8:
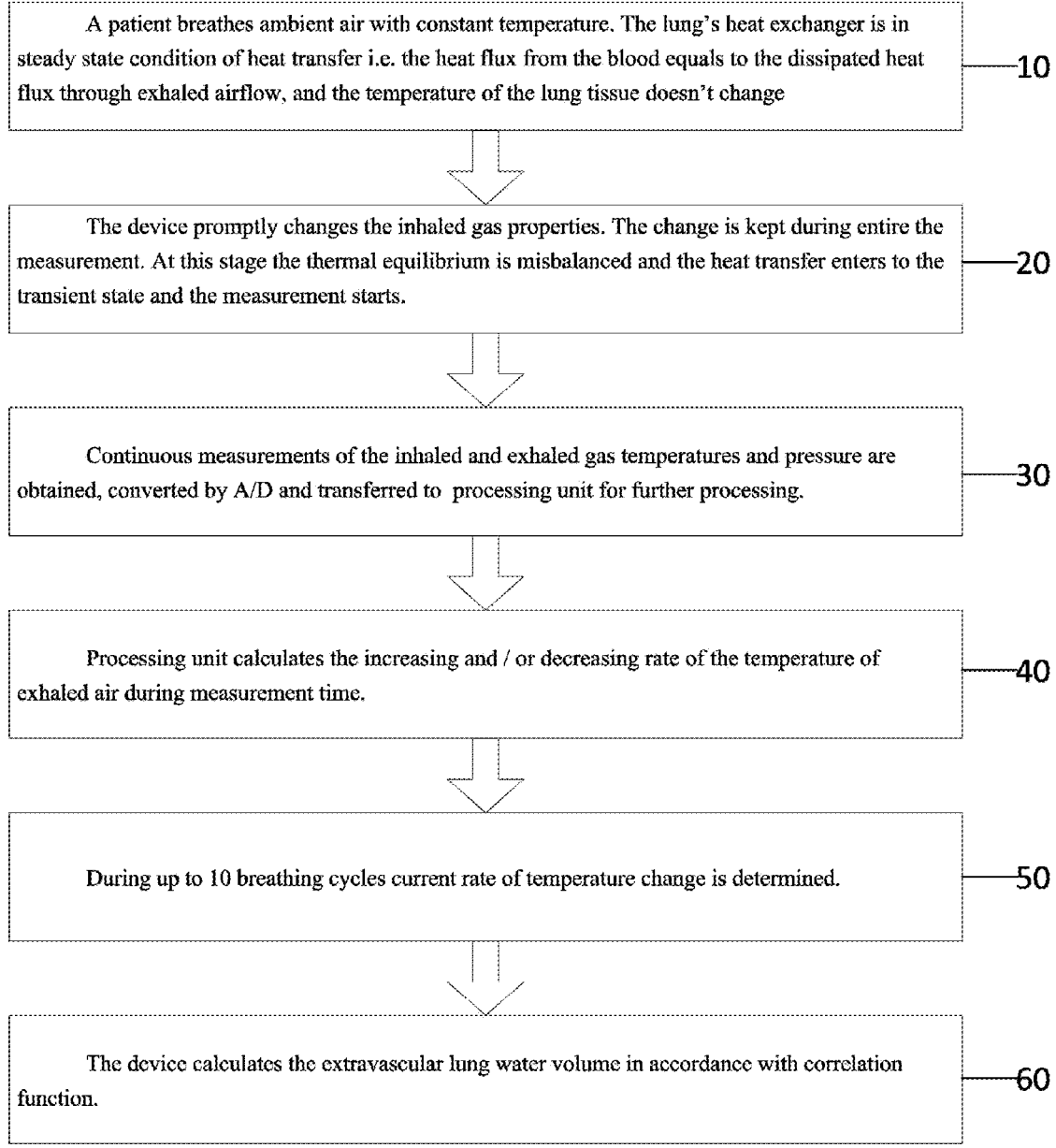
FIG. 8 shows a method for measuring and for processing extra vascular lung water in a spontaneously breathing patient, in accordance with some embodiments of the disclosed subject matter.

FIG. 8 shows a method for measuring and for processing extra vascular lung water of spontaneously breathing patient, in accordance with some embodiments of the disclosed subject matter.

At block 10, a patient breathes ambient air with constant temperature. The lung's heat exchanger is in steady state condition of heat transfer i.e. the heat flux from the blood equals to the dissipated heat flux through exhaled airflow, and the temperature of the lung tissue doesn't change;

At block 20, the device promptly changes the inhaled gas properties or patient changes the breathing parameters such as breathing rate and/or tidal volume. The change is kept during entire the measurement. At this stage the thermal equilibrium is misbalanced and the heat transfer enters to the transient state and the measurement starts.

At block 30, continuous measurements of the inhaled and exhaled gas temperatures and pressure are obtained, converted by A/D and transferred to processing unit for further processing.

At block 40, processing unit calculates the decreasing or increasing rate of the temperature of exhaled air during measurement time.

At block 50, during up to 10 and at least 5 breathing cycles, measured rate of temperature change is determined At block 60, the device calculates the difference between normal value of decreasing or increasing rates and the amount of extravascular lung water in accordance with correlation function that is described in FIG. 7.

Figure 9:
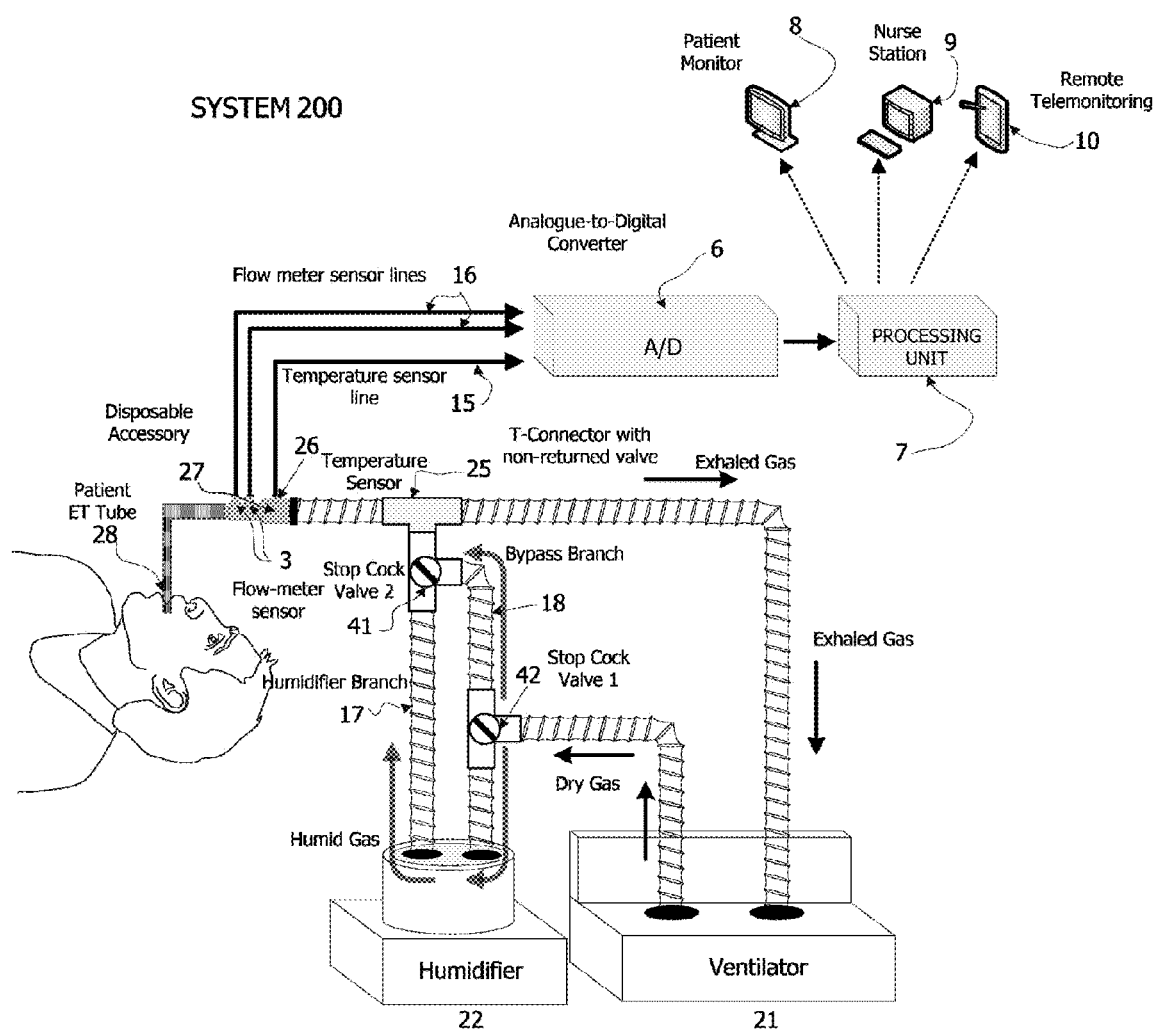
FIG. 9 shows a schematic diagram of system for measuring and processing extra vascular lung water in ventilated patients, in accordance with some embodiments of the disclosed subject matter.
Figure 10:
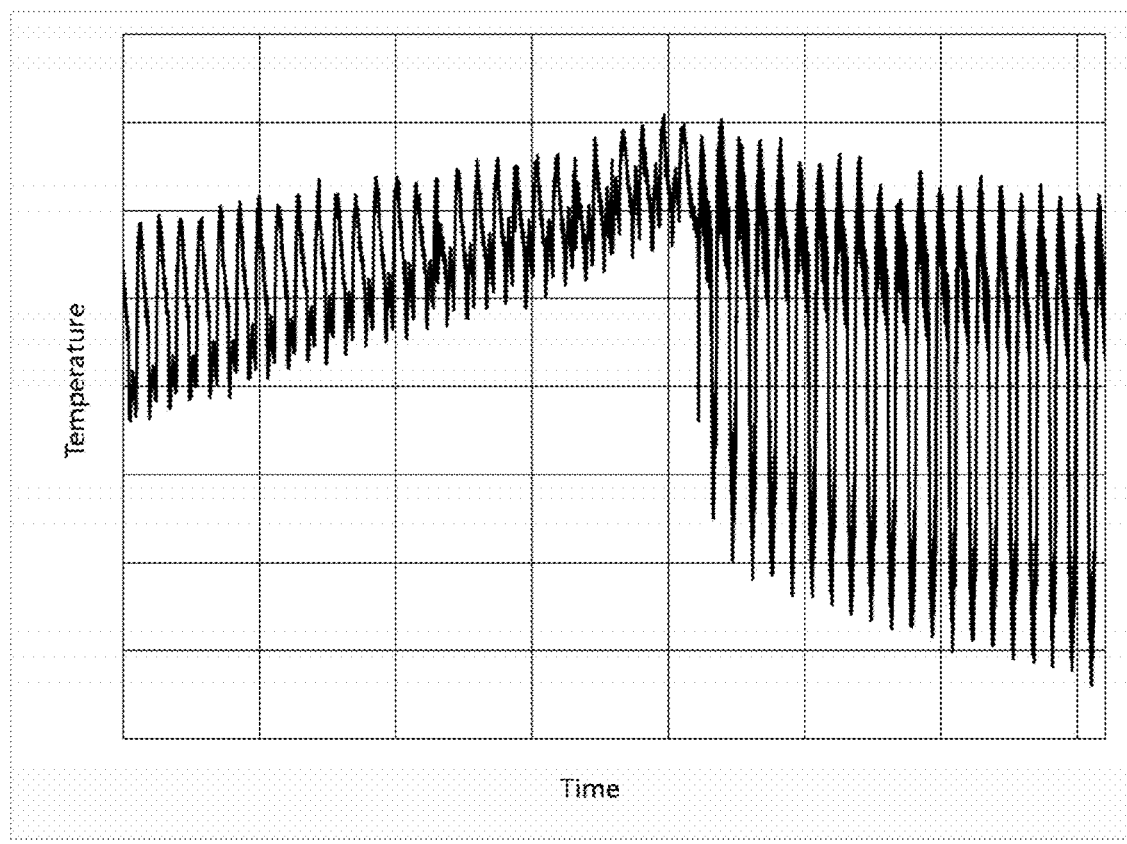
FIG. 10 shows typical measured curve of temperature of inhaled and exhaled gas, in accordance with some embodiments of the disclosed subject matter.

FIG. 9 shows a schematic diagram of system 200 for measuring and processing extra vascular lung water in ventilated patients, in accordance with some embodiments of the disclosed subject matter. In this case, the typical measured temperature signal is as shown in FIG. 10. This temperature signal represent two processes: heating and cooling of lungs. Corresponded pressure drop changes signal shown in FIG. 11. The pressure prop changes signal represents flow rate of inhaled and exhaled air. The curve is used for the determination of the beginning breathing cycle time points [601] and the end breathing cycle time points [602] of the breathing cycles. The time points found by using the pressure drop curve are used in order to determine the time points where the temperature of exhaled air is processed.

Humidifier [22] controls the temperature and humidity properties of inhaled gas. Ventilator [21] controls breathing pattern tidal volume and respiratory rate. During a heating phase the patient is ventilated with warm and humid gas until the difference between temperatures of inhaled and exhaled gases becomes small enough. During the cooling phase the ventilation is switched to supply gas of ambient temperature and humidity.

The system includes also a disposable accessory [27] with incorporated gas temperature sensor [26], flow meter [3] which is based on measurement of pressure drop or any other sensor, allowing determination of gas flow. Flow meter and temperature signals are transferred via temperature sensor line [15] and flow meter sensor lines [16] and captured by an analog-to-digital converter [6], which transfers the converted data to the processing unit [7]. To ensure the separation of inhaled and exhaled gases' flows, there is T-connector with incorporated non-returned valve [25] installed in the gas supplying system.

A patient ventilated through the endotracheal tube [28]. Stop Cock valves [41-42] rout the inhaled gas between Humidifier branch [17] to provide warm and humid gas, and Bypass branch [18] to provide gas of ambient temperature and humidity.

According to some embodiments, the processed data is stored and displayed on bedside computer and displayed on Patient Monitor [8]. According to some other embodiments, the reprocessed data is stored in Hospital Information System in appropriate format (for example DICOM-compatible) and displayed on nurse/doctor working station [9]. According to some other embodiments the processed data is sent to remote telemedicine center [10] for further processing.

FIG. 10 shows measured curve of temperature of inhaled and exhaled gas, in accordance with some embodiments of the disclosed subject matter. At the beginning of the measurement, the ventilation is switched to pass the inhaled air through the humidifier where it is heated. Therefore the temperature of the inhaled and the exhaled air increases. When the temperature difference between the inhaled and the exhaled air is small enough the ventilation switched to ambient air and the temperature of inhaled and exhaled air decreases.

Figure 11:
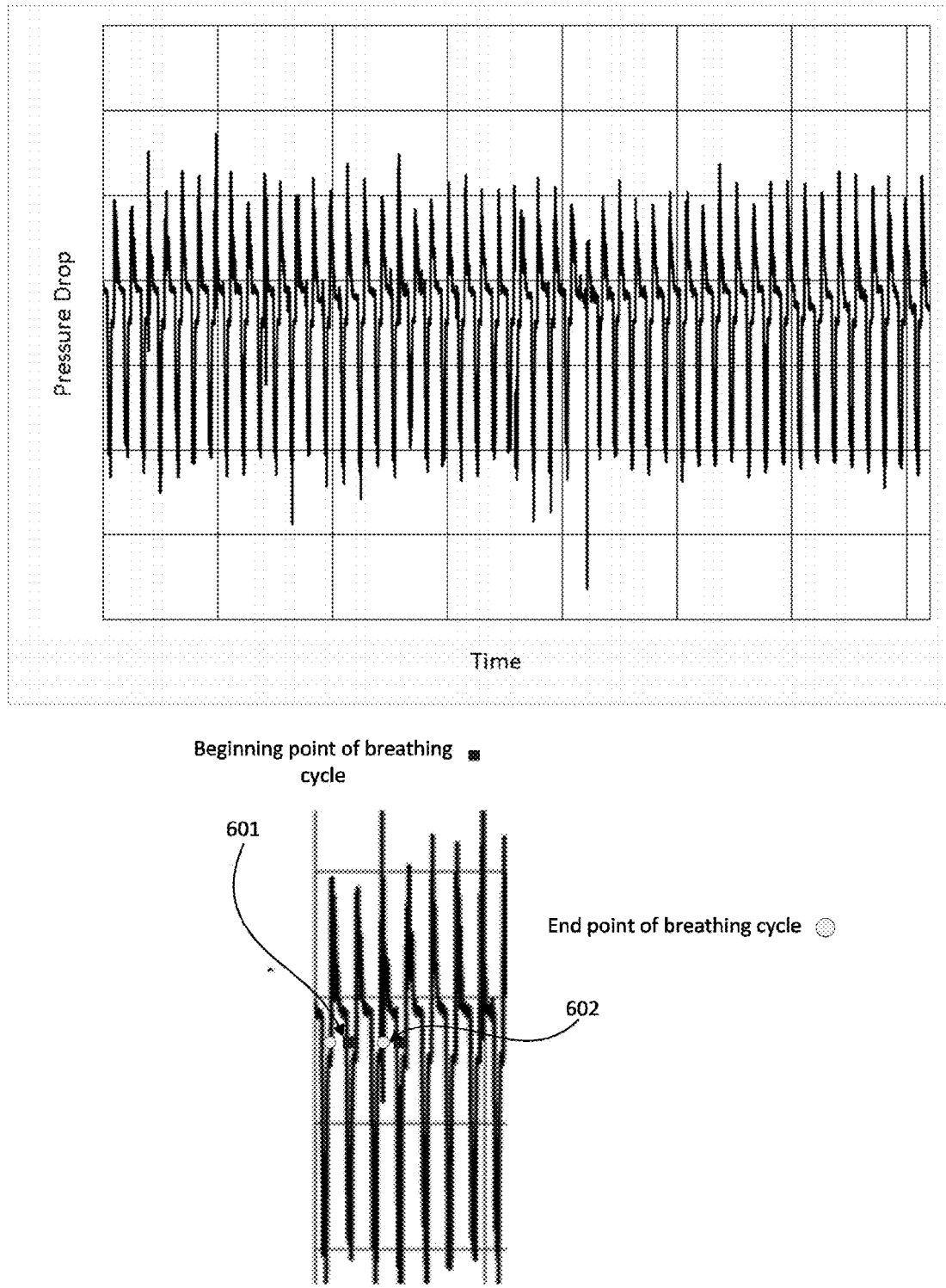
FIG. 11 shows a typical measure curve of pressure drop changes of inhaled and exhaled gas measure during breathing, in accordance with some embodiments of disclosed subject matter.

FIG. 11 shows typical a measured curve of pressure drop which presents air flow rate measure during a heating and a cooling; in accordance with some embodiments of disclosed subject matter. The signal of pressure drop allows to determine the time points of beginning and end of each breath cycle in order to find the temperature which is corresponded to specified temperature of exhaled air.

FIG. 12 shows a method for determination extra vascular lung water for ventilated patients, in accordance with some embodiments of the disclosed subject matter.

At block 101, which is performed at the beginning of measurement, the gas supplying system is switched to provide gas warm and humid through a humidifier instead of gas with ambient temperature and humidity in order to heat the lung tissue. During the heating, temperatures of inhaled, exhaled gas and the patient lung tissue continuously increase.

At block 102, which is performed when the difference between temperatures of inhaled and exhaled gases becomes small enough or when enough number of breathing cycles are recorded during the heating, the gas supplying system is switched to provide gas with ambient temperature and humidity in order to cool of the lung tissue. As a result, the temperature of inhaled and exhaled gas and patient lung tissue correspondingly decrease.

At block 103, continuous measurements of the inhaled and exhaled gas temperatures and gas flow, which are performed entire time of the heating and the cooling described in block 102 and 103, are obtained, converted by A/D and transferred to processing unit for further processing.

At block 104, processing unit calculates the increasing and decreasing rates of the temperature of exhaled air during measurement time.

At block 105, during at least 10 breathing cycles measured rate of temperature change is determined At block 106, the system calculates the difference between normal value of increasing and decreasing rates and the extravascular lung water volume in accordance to correlation function.

FIG. 13 shows correlation between measurement of extravascular lung water by conventional thermo-dilution method and by the non-invasive method for extra vascular lung water measurement according to embodiments of the disclosed subject matter. As it can be observed the measured value by noninvasive method has good correlation with gold standard value. Around the gold standard values presented error-bars denote accuracy of ±10%.

It will be evident to those skilled in the art that the invention is not limited to the details of the foregoing illustrative embodiments and that the present invention may be embodied in other specific forms without departing from the spirit or essential attributes thereof. The present description is therefore to be considered in all respects as illustrative and not restrictive.

What is claimed is:

1. A non-invasive method for determining an extravascular lung water volume in a patient, comprising:
    providing a flow meter and a temperature sensor associated with a mouthpiece, and a processor that is part of, or connectable to, the flow meter and temperature sensor;
    continuously measuring, with the flow meter, first sensing data and continuously measuring, with the temperature sensor, second sensing data, wherein the first sensing data is indicative of a flow of an inspired and an expired gas at an entrance of a patient's upper respiratory tract through the mouthpiece, while a property of said inspired gas or a breathing parameter is controllably changed during said measurements, and wherein the second sensing data is indicative of temperatures of said inspired and said expired gas at the entrance of the patient's upper respiratory tract through said mouthpiece during said continuous measurements;
    processing said first sensing data to determine time points corresponding to ends of expiration phases during a predetermined number of breathing cycles;
    processing the second sensing data to obtain data indicative of a difference between a temperature of said expired gas temperature and a temperature of said inspired gas at said time points corresponding to the ends of the expiration phases;
    analyzing said data indicative of the difference to determine a rate of change of the temperature difference, said rate of change being used to determine said extravascular lung water volume; and
    generating output data corresponding to said extravascular lung water volume.

2. The method of claim 1 further comprises changing the property of said inspired gas or the breathing parameter of said patient, the changing comprising:
    providing cool gas for said patient to breathe; or
    providing hot gas for said patient to breathe; or
    providing wet gas for said patient to breathe; or
    providing dry gas for said patient to breathe; or
    changing breathing tidal volume; or
    changing breathing rate; or
    changing breathing gas mixture.

3. The method of claim 1, further comprising calculating the volume of said extravascular lung water as a function of a difference between said rates of change corresponding to a healthy patient.

4. The method of claim 1, wherein said first and second sensors are configured for measuring up to ten breathing cycles of patient.

5. A non-invasive apparatus for measuring extravascular lung water volume in a patient, the apparatus comprising:
    a first sensor [2] configured for continuously measuring a temperature of an inspired gas and a temperature of an expired gas at an entrance of an upper respiratory tract of a patient via a patient's mouthpiece, and for generating first sensing data; and
    a second sensor [3] configured for measuring a flow of the inspired gas and a flow of the expired gas at the entrance of the upper respiratory tract of the patient, via the patient's mouthpiece, and for generating second sensing data; and
    a processing unit configured for:
        receiving said first sensing data and said second sensing data, while properties of said inspired gas or breathing parameters are controllably changed during said measurements;
        processing said second sensing data to determine time points corresponding to ends of expiration phases during at least a predetermined number of breathing cycles;
        processing the first sensing data to obtain data indicative of a difference between a temperature of said expired gas temperature and a temperature of said inspired gas temperature at said time points corresponding to the ends of the expiration phases;
        analyzing said data indicative of the difference to determine a rate of change of the temperature difference, said rate of change being used to determine said extravascular lung water volume; and
        generating output data corresponding to said extravascular lung water volume.

6. The apparatus of claim 5 further comprising:
    a humidifier [22] configured to increase a humidity of said inspired gas; and/or
    a dehumidifier configured to decrease the humidity of said inspired gas; and/or
    a heater configured to increase the temperature of said inspired gas; and/or
    a cooler configured to decrease the temperature of said inspired gas.

7. The apparatus of claim 5, wherein said patient is ventilated or non-ventilated.

8. The apparatus of claim 5, wherein said first and second sensors are configured for measuring up to ten breathing cycles of patient.

* * * * *